(12) United States Patent
Maschke (10) Patent No.: US 7,785,261 B2
(45) Date of Patent: *Aug. 31, 2010

(54) CATHETER DEVICE WITH A POSITION SENSOR SYSTEM FOR TREATING A VESSEL BLOCKAGE USING IMAGE MONITORING

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 149 days.

This patent is subject to a terminal disclaimer.

(21) Appl. No.: 11/524,608

(22) Filed: Sep. 21, 2006

(65) Prior Publication Data

US 2007/0066888 A1 Mar. 22, 2007
US 2009/0149739 A9 Jun. 11, 2009

Related U.S. Application Data

(63) Continuation-in-part of application No. 10/989,167, filed on Nov. 15, 2004, and a continuation-in-part of application No. 11/055,868, filed on Feb. 11, 2005.

(30) Foreign Application Priority Data

Sep. 21, 2005 (DE) .................. 10 2005 045 071

(51) Int. Cl.
*A61B 8/12* (2006.01)

(52) U.S. Cl. .................. 600/471; 600/407; 600/439; 600/469; 600/478

(58) Field of Classification Search .................. 600/407, 600/424, 427, 439, 466–471, 476–480; 606/159
See application file for complete search history.

(56) References Cited

U.S. PATENT DOCUMENTS

| | | | | |
|---|---|---|---|---|
| 5,830,145 A | * | 11/1998 | Tenhoff | 600/463 |
| 5,897,529 A | * | 4/1999 | Ponzi | 604/95.04 |
| 5,921,926 A | | 7/1999 | Rolland et al. | |
| 6,120,516 A | | 9/2000 | Selmon et al. | |
| 6,148,095 A | * | 11/2000 | Prause et al. | 382/131 |
| 6,152,878 A | | 11/2000 | Nachtomy et al. | |
| 6,217,527 B1 | * | 4/2001 | Selmon et al. | 600/585 |
| 6,299,622 B1 | * | 10/2001 | Snow et al. | 606/159 |
| 6,673,999 B1 | * | 1/2004 | Wang et al. | 174/36 |
| 7,247,162 B1 | * | 7/2007 | Thornton | 606/200 |
| 2002/0019644 A1 | * | 2/2002 | Hastings et al. | 606/159 |
| 2002/0133057 A1 | * | 9/2002 | Kukuk | 600/101 |
| 2003/0135091 A1 | * | 7/2003 | Nakazawa et al. | 600/113 |
| 2004/0133106 A1 | * | 7/2004 | Kakee et al. | 600/437 |
| 2005/0101859 A1 | * | 5/2005 | Maschke | 600/427 |
| 2005/0113685 A1 | | 5/2005 | Maschke et al. | |

(Continued)

FOREIGN PATENT DOCUMENTS

DE  198 27 460 A1  12/1998

(Continued)

*Primary Examiner*—Brian Casler
*Assistant Examiner*—Jonathan G Cwern (57) ABSTRACT

The invention relates to a catheter device, with a position sensor system, for treatment of a partial or complete vessel blockage under image monitoring, with the catheter device featuring a treatment catheter of a vessel blockage, especially by removal or destruction of plaque and/or expansion of the vessel, which is embodied as an integrated unit, especially as a combination catheter, with an OCT catheter and an IVUS catheter for image monitoring and with the position sensor system.

16 Claims, 6 Drawing Sheets

U.S. PATENT DOCUMENTS

| | | | |
|---|---|---|---|
| 2005/0187541 A1 | 8/2005 | Maschke | |
| 2005/0203553 A1* | 9/2005 | Maschke | 606/159 |
| 2005/0222595 A1 | 10/2005 | Maschke | |
| 2006/0015126 A1* | 1/2006 | Sher | 606/159 |
| 2006/0081031 A1* | 4/2006 | Anderson et al. | 73/9 |
| 2006/0217793 A1* | 9/2006 | Costello | 607/122 |

FOREIGN PATENT DOCUMENTS

| | | |
|---|---|---|
| DE | 103 54 496 A1 | 7/2005 |
| DE | 10 2004 008 366 B3 | 9/2005 |
| DE | 10 2004 015 642 B3 | 2/2006 |
| WO | WO 01/11409 A2 | 2/2001 |

\* cited by examiner

CATHETER DEVICE WITH A POSITION SENSOR SYSTEM FOR TREATING A VESSEL BLOCKAGE USING IMAGE MONITORING

CROSS REFERENCE TO RELATED APPLICATIONS

This application claims priority of German application No. 10 2005 045 071.7 filed Sep. 21, 2005, which is incorporated by reference herein in its entirety.

This application is a continuation-in-part of co-pending U.S. application Ser. No. 10/989,167, filed Nov. 15, 2004, and a continuation-in-part of co-pending U.S. application Ser. No. 11/055,868, filed Feb. 11, 2005.

FIELD OF THE INVENTION

The invention relates to a catheter device, embodied with a position sensor system, for treatment of a partial and/or complete blockage of a vessel using image monitoring and to a method for image monitoring in the treatment of a vessel blockage.

BACKGROUND OF THE INVENTION

Diseases of the vascular vessels currently represent one of the most frequent diseases with fatal outcomes. Particular mention should be made here of coronary infarction caused by diseases of the coronary vessels. Arteriosclerotic plaque results in a blockage of the coronary vessels, which can take a more or less serious form.

In recent years different methods for treating such narrowings of for example the coronary vessels or at other points in the vessel system have emerged. In such cases the attempt is made to remove the plaque or to destroy it and/or to expand the vessel in order to remedy the closing-off of the vessel in this way. Interventions of this type for treating partly or completely blocked vessels are mostly carried under x-ray control with an angiography system. However in such cases the vessels involved, such as the coronary vessels for example, only appear as a two-dimensional silhouette. To make the vessel clearly visible additional contrast means must be injected into the vessel, and if for example the vessel is completely blocked, these means do not reach all areas of the vessel. In such cases the problem arises of some patients suffering from contrast means allergies or of the contrast means producing a hot feeling. In addition to this it is possible for the patient to suffer radiation damage.

On the other hand, because of the very restricted imaging, even with the provision of contrast means, it is very difficult for the medical personal to differentiate between plaque and vessel wall during the intervention. This increases the risk or removing or destroying tissue at the wrong places, so that injury to the vessel wall can result for example.

In as far as attempts have been made to rectify these types of problem by additional image monitoring as well as x-ray monitoring there has previously been the problem that, depending on the type of additional image monitoring, only a restricted local resolution or a good resolution only in the local area but not an entirely satisfactory representation can be achieved.

SUMMARY OF THE INVENTION

The underlying object of the invention is thus to specify a catheter device which is improved with regard to the above-mentioned problems.

To achieve this object a catheter device of the type stated at the start is provided, featuring a catheter for treatment of the vessel blockage, which is embodied as an integrated unit with an OCT catheter and an IVUS catheter for image monitoring and with the position sensor system.

The abbreviation OCT stands for "Optical Coherence Tomography", of which the basic principle is based on the Michelson interferometer. OCT catheters allow image data to be recorded which allows a very good local resolution particularly in the local area.

If such a catheter is introduced separately into the vessel, the problem which arises is that for further treatment of the vessel blockage with the treatment catheter the separate OCT catheter must be withdrawn again from the vessel each time in order to subsequently introduce the treatment catheter.

This is avoided by the inventive catheter device in which the OCT catheter is embodied as a combination catheter with the treatment catheter in one integrated unit.

In addition the integrated unit features an IVUS catheter which is based on the technique of intravascular ultrasound and with which additional image data can also be obtained. This makes it possible, not only to map the state of the lumens of vessels but also to create an image of the vessel walls. The ultrasound method alone however only offers a restricted local resolution. If an IVUS catheter is embodied as a separate catheter, like the OCT catheter, this has to be additionally introduced and once again removed from the vessel before the introduction of the treatment catheter, which makes treatment more difficult and imposes greater strain on patients. This is avoided by the inventive integrated solution.

A conventional IVUS system is described for example in DE 198 27 460 A1, whereas the use of OCT technology is known from 01/11409 A2 or U.S. Pat. No. 5,921,926.

In the inventive catheter device these two options of imaging by means of an OCT catheter and an IVUS catheter are integrated into the treatment catheter so that a combination catheter is embodied for treatment and image monitoring. In addition a position sensor system is provided which enables precise localization of the catheter device in the body of the patient. Thus an integrated combination with which an optimum diagnostic imaging and minimally invasive medical treatment becomes possible replaces the previous part or individual solutions. The treatment catheter enables the device to dissolve the vessel blockage, and simultaneously through different imaging methods OCT and IVUS, enables it to provide a good visibility of the catheter in relation to the vessel, to which end the position sensor system for locating the device is additionally used, in order to create images with high spatial resolution in the local area and remote area of the vessel blockage.

The image information of the OCT and IVUS images can be combined in this case, for example for creating overlay images, with a combination with data from conventional x-ray monitoring or similar also being possible. Thus two-dimensional or especially also three-dimensional images with high diagnostic quality can be obtained, whereby the embodiment of the device as combination catheter does away with a temporary withdrawal of one or both imaging catheters and a re-introduction of the treatment catheter with the corresponding disadvantages for the patient as well as for the doctor performing the treatment. This means that the previously unknown combination of the two imaging methods OCT and IVUS with a treatment catheter allows optimum treatment of vessel blockages using image motoring, in which detailed image information will be obtained in all imaging areas, i.e. both in the local and also in the remote area.

The OCT and the IVUS catheter in this case each feature signal lines which lead to the catheter tip, at which the sensors for the optical coherence tomography or the intravascular ultrasound are provided. The OCT sensor can in this case be embodied as a rotating mirror, on which the light signals sent out for detection of interferences are reflected.

In accordance with the invention the catheter for treating the vessel blockage can be a CTO catheter for treating a complete vessel blockage, especially a pincer-type catheter and/or a radiation-based catheter, or a catheter for treating a partial vessel blockage, especially a laser angioplasty catheter.

The abbreviation CTO here stands for "Chronic Total (Coronary) Occlusion", that is for a complete blockage, especially of the coronary vessels. Expanding pincers, which push the plaque in the vessels apart piece-by-piece and thus allow a step-by-step removal of the vessel blockage, can be used for handling these types of blockages. It is also possible to use high-frequency energy with which the plaque can also be removed.

A further method for treatment of a vessel blockage is what is known as laser angioplasty, in which the plaque is destroyed or removed with a thermal or non-thermal laser using heating of a laser balloon catheter or using an ultraviolet pulsed laser. To enable laser angioplasty to be used a residual lumen is required in the vessel however.

The selection of the sensible type of treatment thus depends on the type of blockage and the blockage geometry, taking into consideration the risks and costs. In each case an expediently-selected treatment catheter as a combination catheter in an integrated unit with position sensors and OCT and IVUS sensors for improved imaging is provided with the inventive catheter device.

The signal lines of the OCT and/or of the IVUS catheter can be routed within the catheter shell of the catheter for treatment of the vessel blockage, especially within a hollow drive shaft of the OCT and/or IVUS catheter. The treatment catheter itself can be embodied in this case as a tubular catheter with a catheter shell with at least one or more lumina. Within this catheter shell of the treatment catheter, which has a rather greater diameter as regards its function, the signal lines for the OCT and the IVUS imaging are routed which connect the OCT and IVUS sensors at the tip of the catheter device to a signal and/or drive unit, if necessary in lumina. Expediently a common drive shaft or separate drive shafts are present for the OCT and the IVUS catheter in order to allow independent movement of the two catheters if necessary. The relevant signal lines are expediently routed in a protected manner where necessary in such a drive shaft embodied with a hollow inner space.

The OCT and/or IVUS catheter and/or a surrounding drive shaft can be embodied to allow them to rotate. If instead of an outer drive shaft only the IVUS or OCT sensor rotates, which is connected to its signal lines in each case, there is no friction between the catheter device and the vessel wall. A rotation of the IVUS or OCT catheter rotates an image sensor embodied for example as a mirror for OCT. Instead of an external drive shaft there can of course be a drive shaft present within an outer catheter shell which can also rotate.

The image sensor of the OCT and/or IVUS catheter can be arranged in front of or behind a treatment unit, especially a pair of pincers or a coil or a laser lens, of the catheter for treatment of a vessel blockage. Depending on the type of arrangement for example in front of or behind a coil for creating high-frequency energy for plaque removal, images can be created which show the removal of the plaque for example or the front area of the vessel in which the radiation energy of a laser is already operating or the pincers to remove plaque in a further operation. Thus different information can be obtained as regards a further treatment sequence or the assessment of a treatment just performed or still in progress.

The treatment unit can furthermore feature an opening for feeding through a movable drive shaft and/or the signal lines of the OCT and/or of the IVUS catheter. When such an opening exists it is possible to place the image sensors in front of or behind pincers or a laser lens or such like, as required, by feeding them through the opening for the hollow drive shaft and/or the signal lines or sensors. Thus the imaging with the combined catheter device is not adversely affected by the treatment unit, but comprehensive imaging of the entire treatment area is also possible without removing the treatment unit.

The catheter device can feature at least one transparent exit area for the ultrasound of the IVUS catheter and/or the light of the OCT catheter. Thus for example a surrounding catheter shell of the device can feature one or more transparent exit windows in the area of its tip which are transparent for infrared light or ultrasound and thus allow imaging. It is of course also conceivable for an entirely transparent design or a transparent design not only in the area of the tip of the catheter device to be provided.

For three-dimensional imaging the catheter device can be embodied for rotation and for simultaneous withdrawal and/or advance of the OCT catheter and/or of the IVUS catheter. By rotating the two image sensors or one of the image sensors while simultaneously withdrawing or advancing them it is possible to create three-dimensional images with the combination catheter. In this case it is conceivable on one hand for the two image sensors to rotate and simultaneously for both to be moved in a longitudinal direction, for example both forwards. With an appropriate embodiment of the drive it is however also conceivable for both image sensors to be rotated and for example the OCT catheter to be moved forwards while the IVUS catheter moves backwards or alternately moves slightly forwards and backwards.

In accordance with the invention the position sensor system can be embodied electromagnetically or on the basis of ultrasound. Through position sensors at the tip of the catheter it is possible to obtain an exact three-dimensional representation of the vessel since movement artifacts can be prevented through the size relationships of the catheter relative to the vessel. To do this suitable mathematical methods are used to approximate the center line of the vessel and where necessary of the vessel envelope curve and the corresponding information is combined with the sensor positions. This makes exact, offset-corrected three-dimensional reconstruction possible.

With the aid of electromagnetic position sensors three-dimensional images can be created from the initial two-dimensional OCT or IVUS images which allow a significantly better assessment of the treatment. Parts of the electromagnetic transmitter or also of the receiver can be arranged in the catheter, which in turn leads to the corresponding arrangement of the transmitter or receiver outside the body. For location within space at least one transmitter is assigned to one receiver or vice versa, whereby under some circumstances a combination of two transmitter devices with one receiver or vice versa can be possible, with known angular relationships for example. If the coils of an electromagnetic positioning system are not arranged exclusively orthogonally to each other, but at random angles of for example 60°, the corresponding coil unit can be reduced in size, so that it can be arranged in the catheter without any problems.

The position sensors are expediently arranged in the area of the catheter device tip. This makes location within the area possible, which is also of particular interest for imaging using the OCT or IVUS method. After the installation of an examination device with an inventive catheter device with a position sensor system a calibration is advantageously undertaken and magnetic field sequences are stored as templates.

The catheter device can be embodied for automatic mechanical navigation and/or for magnetic navigation. For an automatic mechanical navigation calculated movements can be reliably and stably implemented using robot technology. In addition magnetic navigation of the combination catheter is also possible, in which the catheter provided with magnets is controlled and driven by an external magnetic field. This can be done using permanent magnets or electromagnets.

Advantageously in accordance with the invention at least one movement sensor for detection of possible patient movements is provided. This enables artifacts caused by such movements to be detected in advance of image computation and excluded from the computations or taken into consideration. A mathematical movement detector can be provided for this purpose or sensors with different operating principles, for example electrical or acoustic sensors or such like can be used. The data can be transmitted over a cable connection or also a wireless connection to an appropriate processing unit. The use of RFID technology is also possible. Movements of organs, caused by a heartbeat for example, can be taken into account using further sensors, by measuring the breathing amplitude or recording an ECG or such like.

In addition at least one physiological sensor can be provided at the tip of the device. This enables micro or nano sensors to be used to measure temperature or pressure or to determine a ph value and such like. In this way additional information is obtained which enables a decision to be made about continuing the treatment or indicates whether the treatment is proceeding without complications.

The catheter device can have a coating for screening and/or improved guidance of the catheter device in the vessel. A screening can prevent magnetic interference fields which may interfere with the recorded signals. One option for such screening is provided by a thin-film layer of nano particles. In addition thermal isolation can be required to protect the electronic components and sensors against a coolant. It is possible using a corresponding coating of the combination catheter to reduce the friction resistance when the catheter is guided or fed through the vessels. Suitable coatings here are a silicon coating or a coating using nano technology materials An image sensor of the OCT catheter can be arranged in a longitudinal direction of the catheter device in front of or behind an image sensor of the IVUS catheter. The OCT sensor which is arranged in front of the IVUS sensor can thus be arranged at the tip of the catheter device in the direction of the treatment to be performed. Alternatively however the order of the sensors can also be reversed. The only decisive factor is how an optimum image monitoring can be achieved in the case concerned.

The catheter device can additionally feature a lumen, especially a separate lumen which is embodied for injection of an ultrasound contrast means. It is thus possible, using a lumen which is present in any event or an additional lumen, to inject an ultrasound contrast means in order to further improve the imaging of the IVUS catheter in this way.

In addition the invention relates to an x-ray device which is embodied with a catheter device as claimed in one of the previous claims. Such an x-ray device thus features a radiation source which is connected to a corresponding system control and generates x-rays with which a patient can be radiologically treated on a corresponding support device. The x-ray images created with the image data and other data which were recorded by the catheter device inserted into the body of the patient with the OCT and IVUS sensor can be combined for evaluation or placed in context via a data bus. The results of the image processing can be presented to the doctor before in the treatment at a display unit of the x-ray device. Thus the treatment of the vessel blockage can be followed using optimum image monitoring, if necessary during the entire treatment.

To this end the x-ray device can be embodied to combine and/or overlay the OCT and/or IVUS data with x-ray data and/or image data of other modalities. The combination catheter images created can be displayed together with the x-ray images using a shared user interface and are thus easily visible at a single defined location for the user so that a rapid and improved diagnosis creation and handling is possible. The very widest range of overlay options of two-dimensional and three-dimensional or two-dimensional and three-dimensional images through to four-dimensional recordings of the angiographic x-ray images and the images of the combination catheter for segmentation, registration and image diffusion produces hitherto unknown diagnostic and handling advantages. The images can be overlaid with images of the modalities such as a sonography, magnetic resonance tomography and such like which have been produced in advance of the treatment or are being created in parallel in a hybrid system, that is in combination with the x-ray device.

Furthermore the invention relates to a method for image monitoring in the treatment of a partial and/or complete vessel blockage by means of a catheter device which features a catheter for treatment of the vessel blockage which is embodied as an integrated unit with an OCT catheter and an IVUS catheter for image monitoring and with a position sensor system. With this method image monitoring is performed within the context of treating a vessel blockage in which a catheter device as described above is used. To this end the catheter is initially introduced under x-ray control and where necessary supplementary supply of contrast means and for example angiographic overview images are created it necessary. After this the images of the electromagnetic position sensors or of another positioning system are created. These images can be overlaid with the images of the overview angiography and the catheter is navigated on the basis of the images through to its target position in the vessel. These steps can in part be undertaken in parallel and automatically without the intervention of the user.

If a desired target position is reached a flushing fluid for optical coherence tomography can be injected it necessary and the blockage of the vessel can be observed by OCT and IVUS images in two or in three dimensions at high resolution. With the aid of the electromagnetic position sensor a three-dimensional reconstruction can be undertaken and a subsequent overlaying with the overview angiography. The treatment unit, that is for example the pincers of the CTO catheter or the laser lens of the laser angioplasty catheter, is placed at the position in the vessel envisaged for the treatment and the placement is checked using the OCT and IVUS data. Subsequently the vessel blockage is opened up or rectified, with the process being repeated until plaque has been removed on all sides over the appropriate length.

After a renewed check by the image monitoring the opened blockage can be subsequently assessed, and if the treatment was successful the catheter can be removed. CTO catheters can in this case, in addition to the use of pincers and high-frequency energy, be based on a therapeutic ultrasound, and produce vibrations, be based on refrigeration technology but also have retractable wires or needles as well as rotation devices and devices for emitting chemical or biological substances.

In addition an application of the method is possible not only in coronary vessels but in general in the vessel-type hollow spaces in human or animal bodies, that its in hollow spaces of organs for example.

The treatment can thus be carried out without the need for certain method steps such as the removal and reintroduction of imaging catheters. In addition only the combination catheter is required for treatment, which means that the end effect is to have a single catheter compared to the previously used separate catheters. Good images can be generated in the local area using OCT imaging whereas IVUS imaging makes possible a good imaging in the surrounding vessel layers. Three-dimensional images can be reconstructed with the aid of the position sensor system and the doses of X-ray radiation applied can be reduced if necessary. As well as additional information about the blockage and the plaque the correct position, especially of the treatment unit, can be better checked.

BRIEF DESCRIPTION OF THE DRAWINGS

Further advantages and details of the invention emerge with reference to the following exemplary embodiments as well as the drawings. The Figures show.

DETAILED DESCRIPTION OF THE INVENTION

Figure 1:
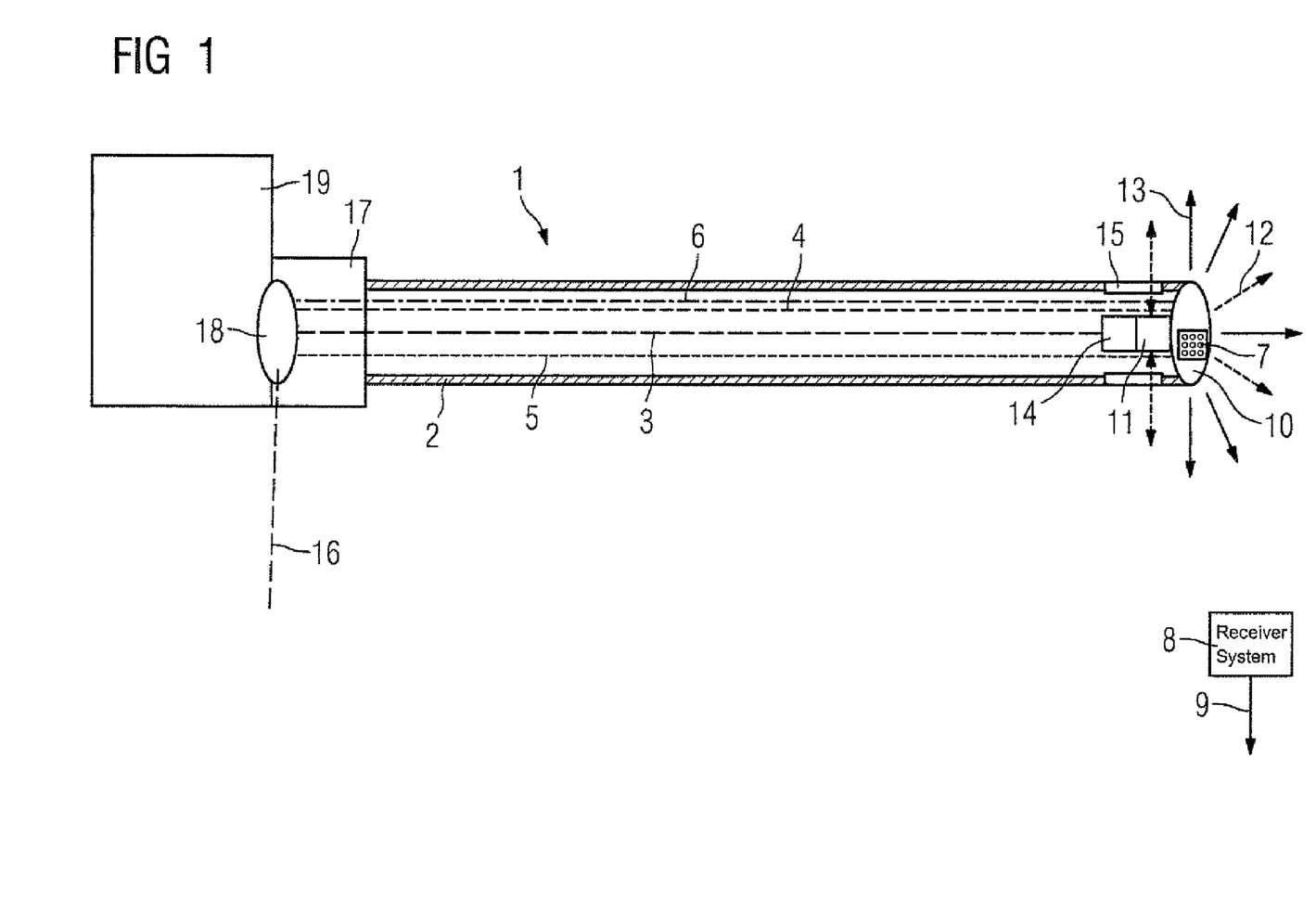
FIG. 1 an inventive catheter device with a laser angioplasty catheter.

FIG. 1 shows an inventive catheter device 1 with a laser angioplasty catheter. The inventive catheter device 1 features a hollow flexible drive shaft 2 in which an OCT signal line 3 and an IVUS signal line 4 are integrated. The OCT signal line 3 is embodied as a glass fiber line in this case. In addition a signal line 5 of the position sensor system which is embodied as an electromagnetic sensor system, and a signal line 6 for the laser energy for performing the laser angioplasty are arranged in the flexible drive shaft 2, with said lines being optical fibers. Thus the surrounding drive shaft 2 produces an integrated unit and which embodies a combination catheter which replaces previously used separate catheters, with the benefit of better image monitoring and treatment of vessel blockages.

A preferred embodiment is an embodiment not shown here in which the drive shaft 2 does not rotate but only the IVUS and the OCT sensor, in order where necessary to avoid friction between the catheter device and the inner wall of the vessel and at the same time effect a rotation of an OCT sensor.

The signal line 5 of the electromagnetic position sensor system leads to antennas 7 arranged at the tip of the catheter device 1, which are arranged in the x, y and z direction and which are merely shown schematically here. The antennas 7 interact with an emitter and/or receiver system 8 outside the body, which in its turn features position sensors or detectors. From here the data, as indicated by the arrow 9, is forwarded via a corresponding interface to a position detection unit.

A lens 10 for emitting laser light or laser energy, which is used for the treatment of the vessel blockage, is activated via the signal line 6. The lens 10 is embodied to be partly transparent for ultrasound in this case so that the ultrasound signals of an IVUS sensor 11, which are indicated here by dashed arrows 12, can penetrate the lens 10. The lens 10 emits the energy forwards or sideways, as shown here by the arrows 13.

An OCT sensor 14 connected to the OCT signal line 3 is embodied as a rotating mirror, whereby the OCT sensor 14 as well as the IVUS sensor 11 is arranged in the direction of advance of the catheter device 1 behind the lens 10. A transparent exit window 15 of the surrounding drive shaft 2 is provided in the area of the OCT sensor 14 or of the IVUS sensor 11 through which the infra-red light and ultrasound to make the imaging possible can emerge. The OCT sensor can, in an alternative not shown here, also be embodied as a rotating shaft on which a light exit or light entry windows present.

In the rear area of the catheter device 1 there is additionally a connection 16 for introducing a contrast means and/or flushing fluid. Operation of the catheter device 1 is made possible via a mechanical connection system 17 and a rotation coupling 18 for the connections. The catheter device 1 can in this case be advanced and withdrawn while a rotational movement for example of the OCT sensor is occurring. Finally the signal and/or drive unit 19 is connected downstream which is used to create the movement as well as to generate signals and detect signals.

Thus a laser angioplasty treatment of a vessel blockage can be undertaken with the inventive combination catheter using optimum image monitoring by OCT and IVUS in combination with electromagnetic position sensors.

Figure 2:
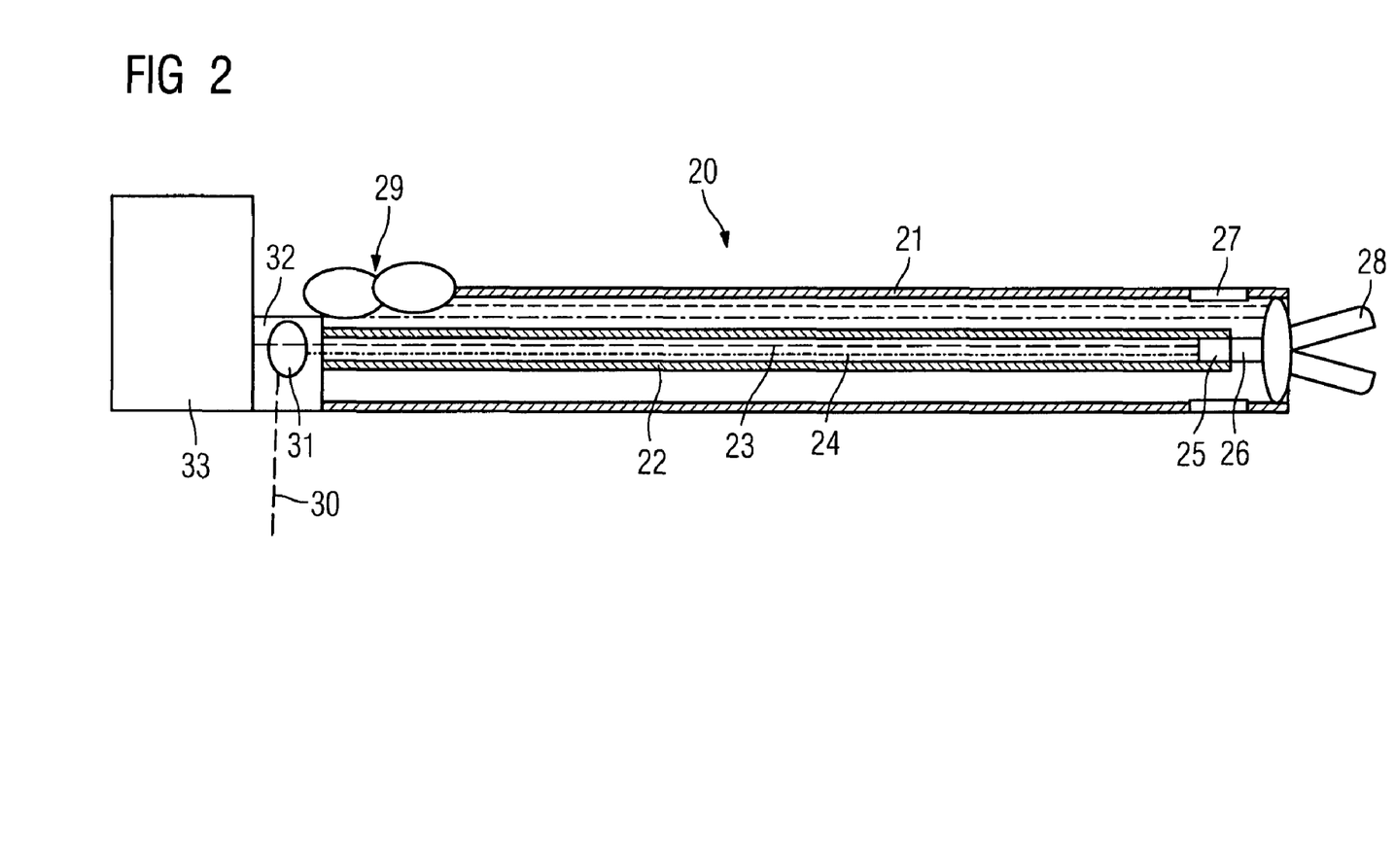
FIG. 2 an inventive catheter device with a pincer-type CTO catheter.

FIG. 2 shows an inventive catheter device 20 with a pincer-type CTO catheter. Here, in addition to a tubular catheter shell 21, a hollow flexible drive shaft 22 is again provided in the inner area of the catheter shell 21 in which an OCT signal line 23 as well as an IVUS signal line 24 are integrated. Signal lines 23 or 24 lead to an OCT sensor 25 which is embodied as a mirror, and to an IVUS sensor 26 arranged before it in the direction of the treatment to be performed. The catheter shell 21 features a transparent window ring 27 in its front area through which the light or ultrasound of the OCT sensor 25 and of the IVUS sensor 26 can escape.

For treatment of the complete vessel blockage "pincers" 28 are arranged at the tip of the catheter device 20 with which the plaque in the vessels can be pushed away piece-by-piece, in order to remove the complete vessel blockage in stages. In the rear area of the catheter device 20 is a mechanical device 29 for actuating the "pincers" 28 of the pincer-type catheter. In addition there is again a connection 30 for bringing in contrast media and/or flushing fluid, and also a rotation coupling 31 and a mechanical connection system 32. The imaging catheter is activated via a signal and/or drive unit 33. The recorded image signals are additionally fed back to the signal and/or drive unit 33 via the signal lines 23, 24 for further processing in order to create image recordings from them. The position sensor system also present is not shown here for reasons of clarity.

Figure 3A:
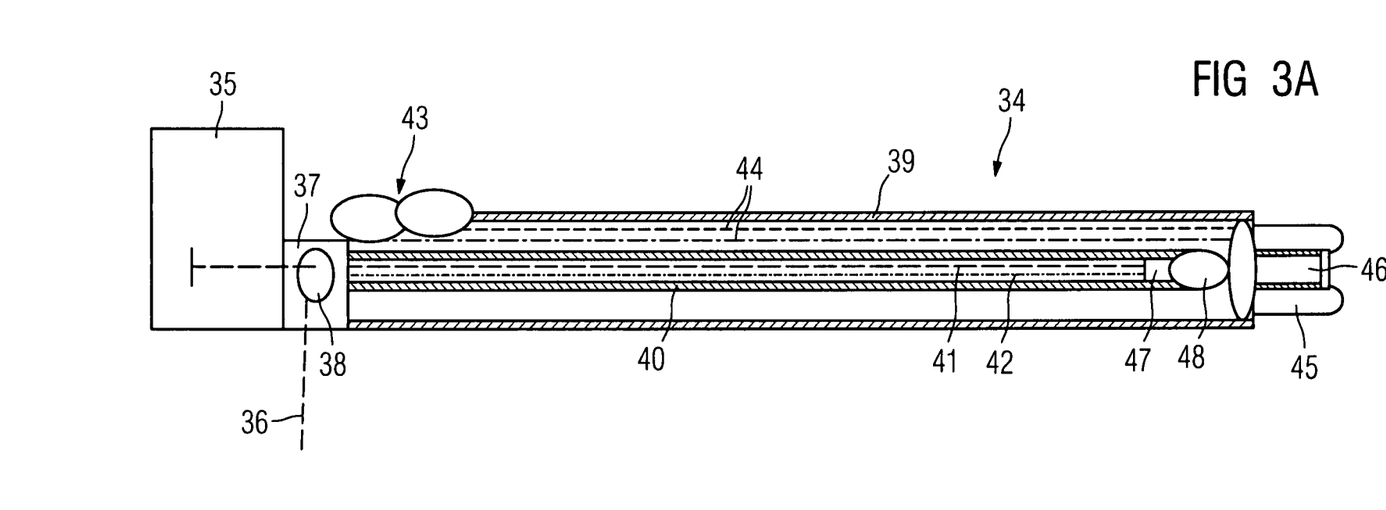
FIG. 3A an inventive catheter device with a pincer-type CTO catheter which features an opening for the OCT and IVUS sensor, FIG. 3B a cross-section of the tip of the catheter device shown in FIG. 3A, FIG. 4A an inventive catheter device with a high frequency-based CTO catheter and a drive shaft, FIG. 4B an inventive catheter device with a high-frequency-based CTO catheter and a rotatable OCT and IVUS catheter, FIG. 5 an inventive x-ray device with a CTO catheter device and FIG. 6 a schematic diagram for sensor readout when executing an inventive method with the x-ray device shown in FIG. 5.

FIG. 3A shows an inventive catheter device 34 with a pincer-type CTO catheter which features an opening for transmission of the OCT and IVUS sensors in its tip area. The catheter device 34 is activated via a signal and/or drive unit 35 which enables imaging operation. As well as a connection 36 for bringing in contrast media and/or flushing fluid, a mechanical connection system 37 for connection with the front part of the catheter device 34 and a rotation coupling 38 for the connections of the catheter device 34 are provided.

A hollow flexible drive shaft 40 is arranged in a catheter shell 39 in which the IVUS signal line 41 and the OCT signal line 42 are routed. A "pincer" 45 for dissolving the constriction of the vessel can be operated via a mechanical device 43 with corresponding lines 44. The "pincer" 45 features an opening 46 through which an OCT sensor 47 and an IVUS sensor 48 can be moved, in order to record image data in advance of the "pincers" 45. In the arrangement of the OCT sensor 47 or of the IVUS sensor 48 images can also be recorded here via a corresponding transparent embodiment of the catheter shell 39. Thus the area for treatment can be recorded over a wide area and thereby the treatment or the progress of the treatment better assessed.

Figure 3B:
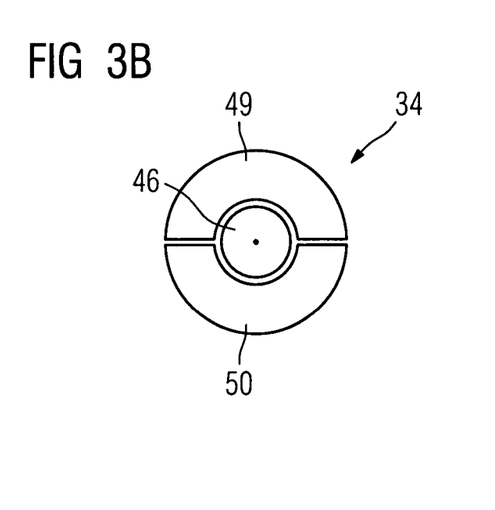

FIG. 3B shows a front view of the tip of the catheter device 34, in which an upper half 49 and a lower half 50 of the "pincers" 45 can be seen. The opening 46 is shown in the central area, through which the sensors 47 and 48 can move to record image data.

Figure 4A:
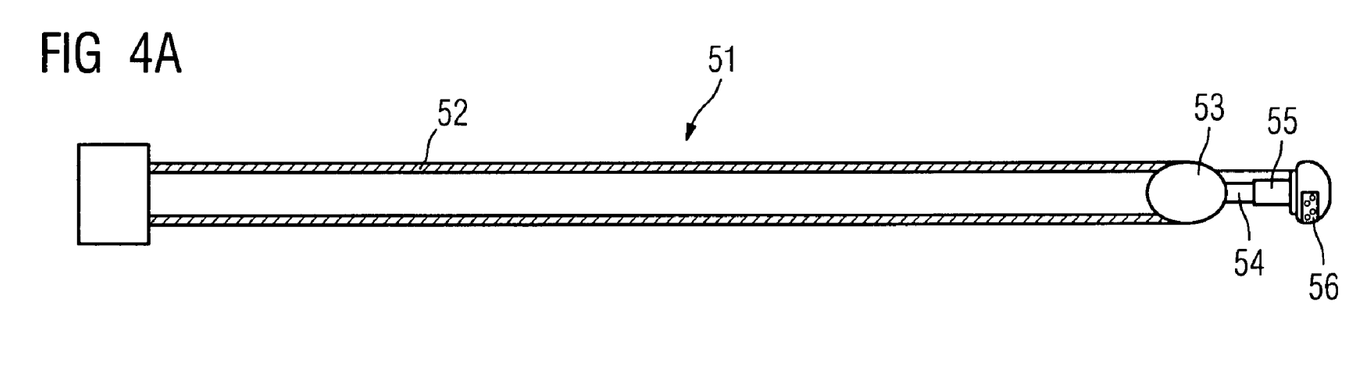

FIG. 4A finally shows an inventive device 51 with a high-frequency-based CTO catheter. The catheter device 51 again features a drive shaft 52 in which the glass fiber line for the OCT sensor as well the lines for the IVUS sensor the electromagnetic position sensor system and the optical fiber for activation of a coil 53 not shown in the drawing are accommodated. An emission of high-frequency energy is possible via the coil 53 in order to remove plaque in the vessel by this method. In the front area of the coil 53 an OCT sensor 54 is arranged, with an IVUS sensor 55 in front of it. In addition an antenna system 56 of the electromagnetic position sensor system is indicated. A vessel blockage can be rectified with the inventive catheter device 51 by emitting high-frequency radiation by means of the coil 53.

Figure 4B:
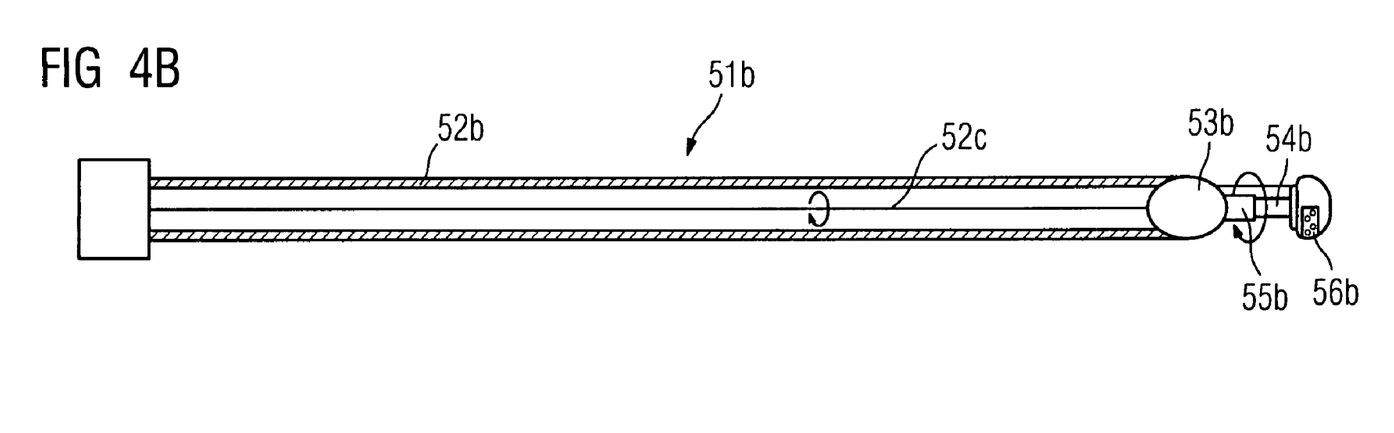

FIG. 4B shows an inventive catheter device 51b with a high-frequency-based CTO catheter and a rotatable OCT and IVUS catheter. The catheter device 51b features a flexible catheter shell 52b which is embodied in a fixed position. A coil 53b allows the emission of high-frequency radiation for plaque removal. In front of the coil 53b an IVUS sensor 55b is initially arranged, in front of which an OCT sensor 54b is connected. The OCT sensor 54b and the IVUS sensor 55b are controlled via the signal lines 52c which are shown in simplified form in this figure. Furthermore an antenna system 56b is again provided for a position sensor system.

The difference from the device depicted in FIG. 4A is that here the catheter shell 52b is not embodied as a rotating drive shaft but that the OCT and the IVUS catheters with their sensors 55b and 54b rotate within the catheter shell 52b, as shown by the arrows in the diagram. This enables damage to the vessel wall in critical areas of the vessel to be avoided, since the rotating section of the catheter device 51b can no longer come into direct contact with the vessel wall.

Figure 5:
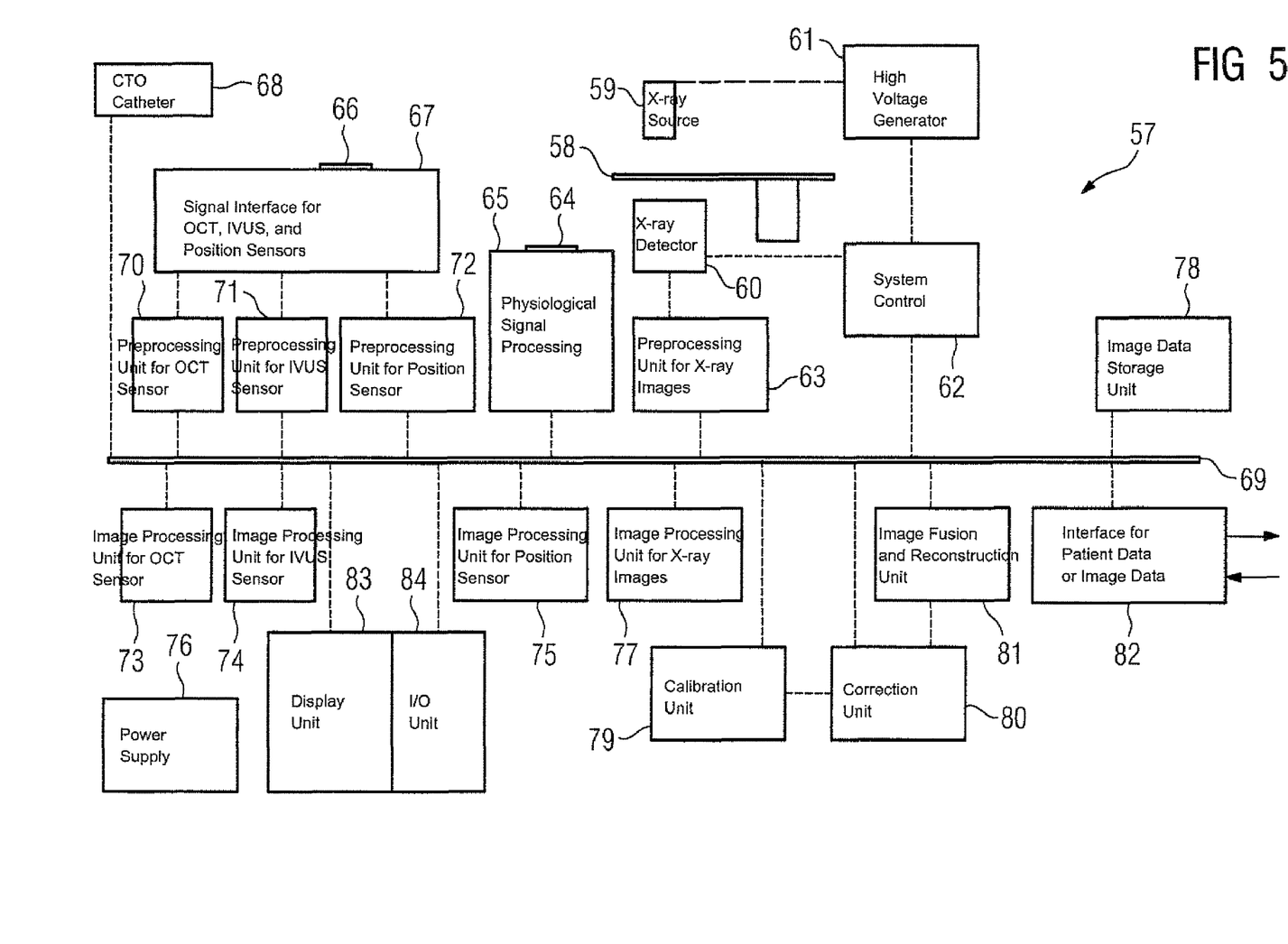

FIG. 5 shows an inventive x-ray device 57 with a CTO catheter device, which is based on sending out high-frequency radiation. A patient not shown in this diagram is supported on a patient table 58 for treatment and radiation is emitted via a radiation source 59 in the direction of the patient table 58. The radiation is produced via a high-voltage generator 61 controlled via a system control 62. Opposite a radiation source 59 an x-ray detector 60 is arranged, which is connected in its turn with a preprocessing unit 63 for x-ray images. In addition a connection 64 is provided for physiological sensors, which is coupled to a physiological signal processing 65 in order to control ECG signals or pulse signals or the breathing and the blood pressure of a patient.

A connection 66 is made via a terminal for the CTO catheter to a signal interface 67 for the actual treatment by OCT, IVUS and the electromagnetic position sensor system. In addition there is a connection for connecting a high-frequency based CTO catheter device 68 and a data bus 69. Another version of the CTO catheter device is alternately possible. There are also preprocessing units 70 to 72 for the OCT images, the IVUS images and the electromagnetic position sensor system provided. The associated image processing units 73, 74 and 75 are also connected to the data bus 69. The power is supplied via a power supply unit 76. Furthermore an image processing unit 77 for the x-ray images is connected to the data bus 69, which features a connection to an image data store 78 for archiving and storing the recorded images. A calibration unit 79 as well as an image correction unit 80 enables interference fields or artifacts of the imaging to be taken into account. The images are fused and reconstructed in an image fusion and/or reconstruction unit 81. In addition there is an interface 82 to patient data or image data system.

The image data obtained from OCT, IVUS and the position sensor system as well as the x-ray images and possible fusion images of the different imaging techniques are shown on a display unit 83 in two dimensions, three dimensions or four dimensions. The display unit 83 is connected to an input 84 for input by a user.

Figure 6:
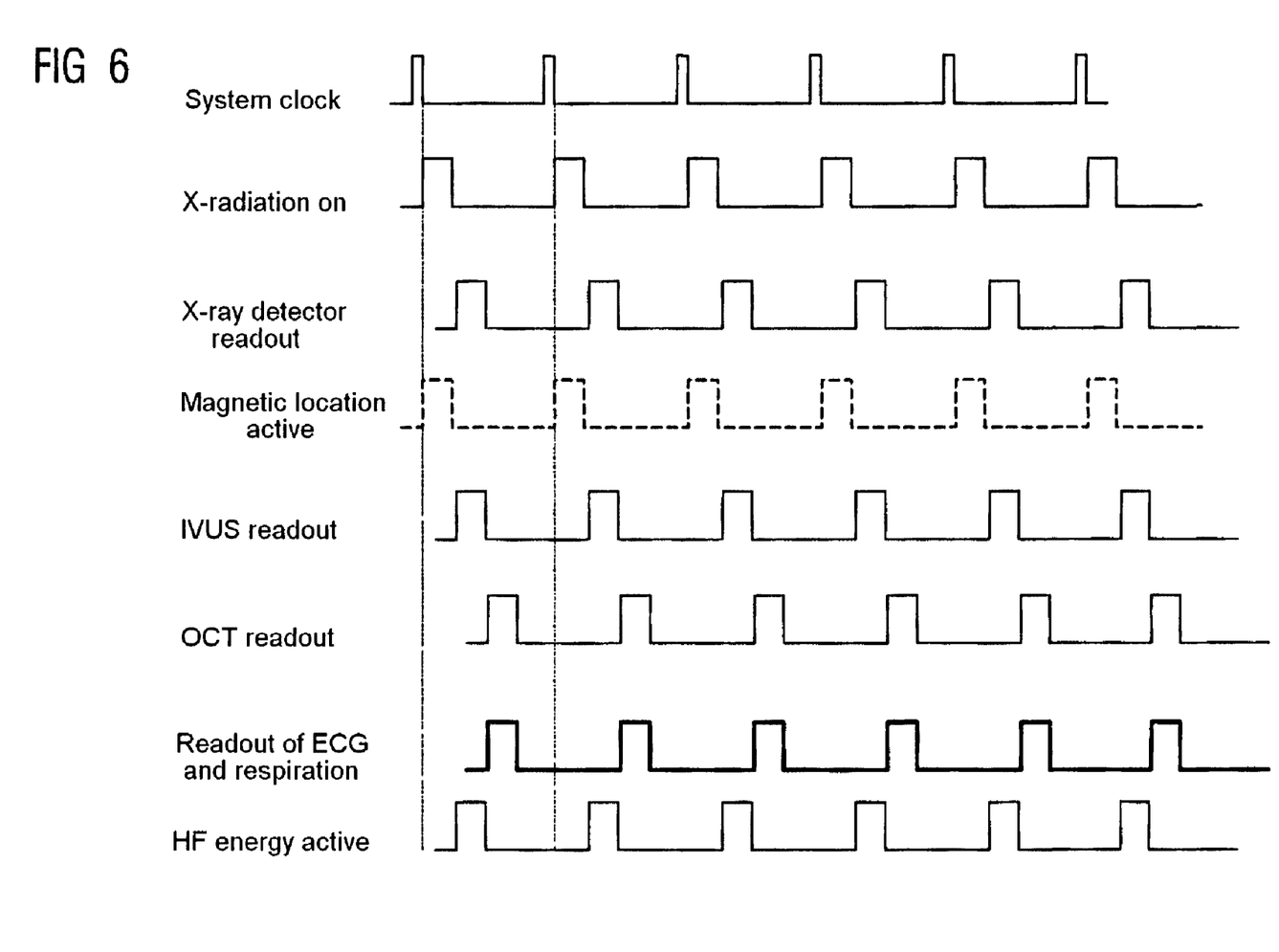

FIG. 6 shows a sketch or sensor readout during execution of an inventive method with the x-ray device 57 of FIG. 5. In this case the sensors of the x-ray device 57 are read out with a partial time offset and clocked. Firstly a system clock is predefined by creating individual system pulses with the pulse generation being followed by the switching of the x-ray radiation and the activation of the magnetic location. After the x-ray radiation is switched of the x-ray detector readout occurs and at the same time the IVUS data is read out. Subsequently the OCT data is read out, with this occurring at the same time as the readout of the ECG and the data for respiration. During the readout of the IVUS data and of the x-ray detector the high-frequency energy which is being emitted to remove the vessel blockage is active. This means that the individual sensor is read out or the components of the catheter device are activated in such a way that a mutual fault can be excluded. The time-offset and clocked readout shown here is to be seen as an example for a readout avoiding interference influences.

The invention claimed is:

1. A catheter device for treatment of a vessel blockage of a patient under an image monitoring, comprising:
   a pincer-type catheter which treats the vessel blockage, said pincer-type catheter arranged at a tip of the catheter device, and including pincers configured to push away plaque of the vessel blockage in stages to remove the vessel blockage;
   a position sensor system which is arranged in the catheter device for locating a position of the catheter device within the patient;
   an OCT catheter and an IVUS catheter which are arranged in the catheter device for the image monitoring;

an image fusion unit coupled to the OCT catheter, the IVUS catheter and the position sensor system; said image fusion unit configured to combine image data from the OCT catheter of a local area to the vessel blockage and image data from the IVUS catheter of a remote area to the vessel blockage into a combined OCT/IVUS image;

an X-ray device configured to combine or overlay the combined OCT/IVUS image with image data of the patient from the X-ray image device, to register the OCT/IVUS image;

wherein said pincers include an opening through which the OCT catheter and IVUS catheter are configured to pass to record an image in advance of said pincers, said opening being formed between an upper half and a lower half of the pincers;

and wherein the catheter device is configured to rotate and simultaneously pull or push the OCT catheter or the IVUS catheter through the opening, to perform a three-dimensional imaging.

2. The catheter device as claimed in claim 1, wherein the pincer-type catheter, the position sensor system, and the OCT catheter and the IVUS catheter are integrated as an integrated unit.

3. The catheter device as claimed in claim 1, wherein the pincer-type catheter is a chronic total occlusion catheter for a treatment of a complete vessel blockage or a catheter for a treatment of a partial vessel blockage.

4. The catheter device as claimed in claim 1, wherein a signal line of the OCT or the IVUS catheter is guided within a shell of the catheter device.

5. The catheter device as claimed in claim 4, wherein the signal line of the OCT or the IVUS catheter is guided within a hollow drive shaft of the OCT catheter or the IVUS catheter, and wherein the OCT catheter or the IVUS catheter or the drive shaft is configured to rotate.

6. The catheter device as claimed in claim 1, wherein an image sensor of the OCT catheter or the IVUS catheter is arranged in front of or behind the pincers, said opening of the pincers is configured for passing through a drive shaft or a signal line or the image sensor.

7. The catheter device as claimed in claim 1, wherein the catheter device comprises a transparent exit area.

8. The catheter device as claimed in claim 1, wherein the position sensor system is an electromagnetic or an ultrasound system and a position sensor is arranged at the tip of the catheter device.

9. The catheter device as claimed in claim 1, wherein the catheter device is configured to navigate mechanically or magnetically.

10. The catheter device as claimed in claim 1, wherein the catheter device comprises a movement sensor which detects a movement of the patient.

11. The catheter device as claimed in claim 1, wherein a physiological sensor is arranged at the tip of the catheter device.

12. The catheter device as claimed in claim 1, wherein the catheter device is coated by a coating.

13. The catheter device as claimed in claim 1, wherein an image sensor of the OCT catheter is arranged in front of or behind an image sensor of the IVUS catheter in a longitudinal direction of the catheter device.

14. The catheter device as claimed in claim 1, wherein the catheter device comprises a lumen for injecting an ultrasound contrast medium.

15. An X-ray device for treatment of a vessel blockage of a patient under an image supervision, comprising:

a patient supporting device;

an X-ray image device which records an X-ray image of the patient;

a catheter device arranged in the X-ray device comprising:
a position sensor system arranged in the catheter device for locating a position of the catheter device within the patient; and
an OCT catheter and an IVUS catheter arranged in the catheter device for the image supervision, said catheter device being configured to rotate and simultaneously pull or push the OCT catheter or the IVUS catheter, to provide image data;

an image processing device which processes the image data from the OCT catheter and the IVUS catheter and an X-ray image data from the X-ray image device, said image processing device configured to combine image data from the OCT catheter of a local area to the vessel blockage and image data from the IVUS catheter of a remote area to the vessel blockage into a combined OCT/IVUS image;

a display unit which displays a result of the image processing device; and wherein the X-ray device combines or overlays the combined OCT/IVUS image with the image data from the X-ray image device, to register the combined OCT/IVUS image.

16. A method for an image monitoring during a treatment of a blocked vessel of a patient, comprising:

providing a pincer-type catheter for treating the blocked vessel, said pincer-type catheter arranged at a tip of the catheter device and including pincers to push away plaque of the vessel blockage in stages to remove the vessel blockage;

arranging a position sensor system for locating a position of the pincer-type catheter within the patient;

arranging an OCT catheter and an IVUS catheter for the image monitoring;

integrating the pincer-type catheter, the position sensor system, and the OCT catheter and the IVUS catheter as an integrated catheter device;

forming an opening in the pincers between an upper half and a lower half of the pincers;

passing the OCT catheter and IVUS catheter through an opening in the pincers to record an image in advance of said pincers;

simultaneously rotating the catheter while pulling or pushing the OCT catheter or the IVUS catheter through the opening, to perform a three-dimensional imaging;

combining image data from the OCT catheter of a local area to the blocked vessel with image data from the IVUS catheter of a remote area to the blocked vessel into a combined OCT/IVUS image; and combining the OCT/IVUS image data with X-ray image data of the patient, to register the OCT/IVUS image.

* * * * *